United States Patent [19]

Langbein et al.

[11] 3,992,542

[45] Nov. 16, 1976

[54] PHARMACEUTICAL COMPOSITIONS CONTAINING AN N-(FURYL-METHYL)-6,14-(ENDOETHANO OR ENDOETHENO)-7α-HYDROXYALKYL-TETRAHYDRO-NOROIPAVINE OR -NORTHEBAINE AND METHOD OF USE

[75] Inventors: Adolf Langbein; Herbert Merz; Gerhard Walther; Klaus Stockhaus, all of Ingelheim am Rhein, Germany

[73] Assignee: Boehringer Ingelheim GmbH, Ingelheim am Rhein, Germany

[22] Filed: Oct. 30, 1975

[21] Appl. No.: 627,208

Related U.S. Application Data

[62] Division of Ser. No. 369,500, June 13, 1973, Pat. No. 3,931,189.

[30] Foreign Application Priority Data

June 21, 1972 Germany............................ 2230154

[52] U.S. Cl. ................................................. 424/260
[51] Int. Cl.² ......................................... A61K 31/485
[58] Field of Search............................ 424/285, 260

[56] References Cited
OTHER PUBLICATIONS
J.A.C.S., 89, 3267 (1967).

Primary Examiner—Stanley J. Friedman
Attorney, Agent, or Firm—Hammond & Littell

[57] ABSTRACT

Pharmaceutical compositions containing as an active ingredient a compound of the formula

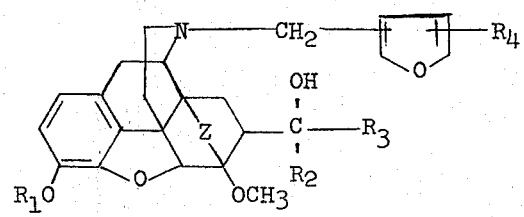

wherein
$R_1$ is hydrogen, methyl or acetyl,
$R_2$ is hydrogen or methyl,
$R_3$ is hydrogen, methyl, n-propyl, phenethyl, or phenyl,
$R_4$ is hydrogen or methyl, and
Z is —CH=CH— or —CH$_2$—CH$_2$—, or a non-toxic, pharmacologically acceptable acid addition salt thereof; and a method of using the same as analgesics and antitussives.

12 Claims, No Drawings

PHARMACEUTICAL COMPOSITIONS CONTAINING AN N-(FURYL-METHYL)-6,14-(ENDOETHANO OR ENDOETHENO)-7α-HYDROXYALKYL-TETRAHYDRO-NOROIPAVINE OR -NORTHEBAINE AND METHOD OF USE

This is a division of copending application Ser. No. 369,500 filed June, 13, 1973, now U.S. Pat. No. 3,931,189 granted Jan. 6, 1976.

This invention relates to novel pharmaceutical compositions containing an N-(furyl-methyl)-7α-hydrdoxy-alkyl-6,14-(endoetheno or endoethano)-tetrahydro-nororipavine or -northebaine or a non-toxic acid addition salt thereof, as well as to a method of using the same as analgesics and antitussives.

THE PRIOR ART

In J.A.C.S. 89, 3267 et seq. (1967), it is disclosed that compound of the formula

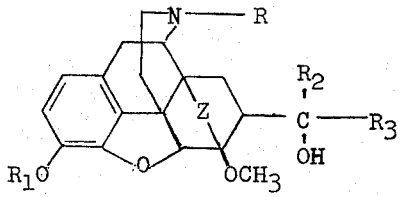

wherein
R is allyl or cyclopropylmethyl
$R_1$ is hydrogen or methyl,
$R_2$ and $R_3$ are hydrogen, allkyl, phenyl or aralkyl, and
Z is —CH=CH— or —CH$_2$—CH$_2$—,
are very strong central analgesics and, in addition, exhibit morphine-antagonistic properties.

THE INVENTION

More particularly, the present invention relates to novel pharmaceutical compositions containing as an active ingredient an N-furylmethyl-7α-hydroxy-alkyl-6,14-(endoethano or endoetheno)-tetrahydro-nororipavine or -northebaine of the formula

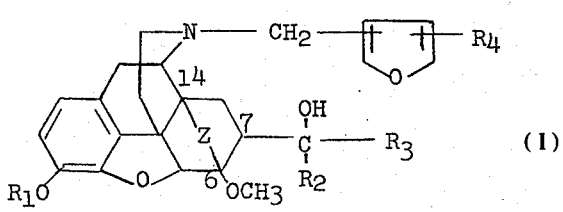

wherein
$R_1$ is hydrogen, methyl or acetyl,
$R_2$ is hydrogen or methyl,
$R_3$ is hydrogen, methyl, n-propyl, phenethyl or phenyl,
$R_4$ is hydrogen or methyl, and
Z is —CH=CH— or —CH$_2$—CH$_2$—,
or a non-toxic, pharmacologically acceptable acid addition salt thereof.

A preferrred subgenus thereunder is constituted by those compositions which contain a compound of the formula I wherein $R_1$ is hydrogen, and the remaining variables have the meanings previously defined.

The compounds may form isomers in the 7-position; "7α" means that the hydroxyalkyl substituent lies below the plane of the paper.

The compounds embraced by formula I may be prepared by the following methods.

Method A

By reacting an oripavine or thebaine derivative of the formula

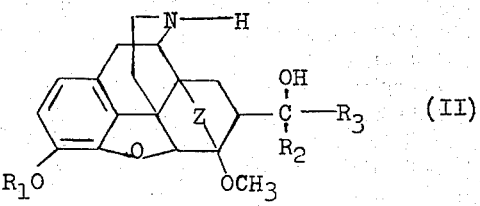

wherein $R_1$, $R_2$, $R_3$ and Z have the same meanings as in formula I, with a furylmethyl derivative of the formula

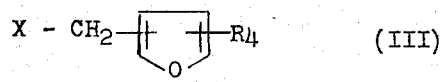

wherein
$R_4$ has the meanings previously defined, and
X is halogen, preferably chlorine, bromine or iodine, alkyl—SO$_2$—O—, aryl—SO$_2$—O— or trialkylammonium, preferably (CH$_3$)$_3$—N—.

The reaction of the compound of the formula II is performed with the calculated amount, or a slight excess thereover, of the furylmethyl derivative of the formula III, optionally in the presence of an acid-binding agent. Examples of suitable acid-binding agents are tertiary amines, such as triethylamine or N,N-dicycylohexyl-ethylamine; alkali metal carbonates, such as sodium carbonate or potassium carbonate; alkali metal bicarbonates, preferably sodium bicarbonate; or alkali metal hydroxides or oxides. The reaction is advantageous carried out in an inert organic solvent medium, such as tetrahydrofuran, dioxane, methylene chloride, dimethylformamide, dimethylsulfoxide or a mixture of two or more of these, preferably mixtures of tetrahydrofuran and dimethylformamide. The reaction temperature may vary within wide limits, but a temperature between 0° C. and the boiling point of the particular solvent medium which is used is preferred. After completion of the reaction, the reaction product is isolated and crystallized by conventional methods.

Method B

By reaction a compound of formula II with formaldehyde and furan of the formula

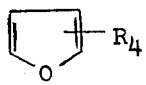 (IV)

wherein $R_4$ has the meanings defined above.

The reaction is carried out in weakly acid solution, especially in an acetic acid solution, and preferably in aqueous 50% acetic acid. Other suitable solvents are water, lower alkanols, tetrahydrofuran, dioxane or mixtures of any two or more of these. The furan of the formula IV is provided in the stoichiometric amount or in slight excess thereover, either dissolved or suspended in the solvent medium. The formaldehyde may be provided in the form of paraformaldehyde or preferably in the form of an aqueous solution in the calculated amount or in excess thereover. The reaction temperature may vary between −10° C. and the boiling point of the particular solvent medium which is employed, but the preferred temperature is 25° C. After completion of the reaction, the reaction product is isolated and crystallized by conventional methods.

Method C

By reducing a compound of the formula

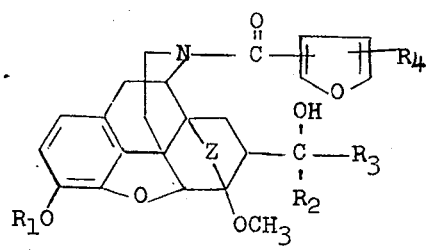 (V)

wherein $R_1$, $R_2$, $R_3$, $R_4$ and A have the meanings previously defined, or, for the preparation of a compound of the formula I wherein $R_2$ is hydrogen, by reducing a compound of the formula

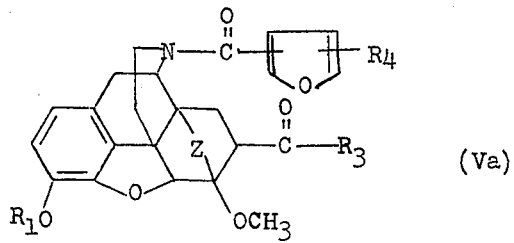 (Va)

wherein $R_1$, $R_3$, $R_4$ and Z have the meanings previously defined.

Among the various suitable reduction methods, the reduction with a complex hydride, in particular with lithium aluminum hydride, is preferably used. Either the calculated quantity or, preferably, an excess of the hydride, advantageously up to double the calculated quantity, is provided. The reduction is advantageously performed in a suitable inert solvent or solvent mixture, such as ethers, but preferably in tetrahydrofuran. The reaction temperature is variable within wide limits. Temperatures between 0° C. and the boiling point of the solvent or mixture of solvents are preferred.

If $R_1$ in formula V or Va is acetyl, the O-acetyl group is split off simultaneously with the reduction of the carbonyl groups, and in this case a compound of the formula I is obtained, wherein $R_1$ is hydrogen. The reaction product is isolated and crystallized by conventional methods.

Method D

For the preparation of a compound of the formula I wherein $R_1$ is methyl or acetyl, by methylating or acetylating, respectively, a compound of the formula I wherein $R_1$ is hydrogen.

The methylation is effected in conventional manner, that is, by reacting the starting compound with a conventional methylating agent, such as diazomethane, a methyl ester of an inorganic acid, preferably dimethylsulfate, or a phenyl trimethylammonium compound.

The acetylation is effected with conventional acetylating agents, such as an acetyl halide, preferably acetyl chloride, or acetic acid anhydride.

The methylation as well as the acetylation is advantageously carried out in the presence of an acid-binding agent, such as pyridine or another tertiary amine, and in the presence of an inert solvent medium, preferably methylene chloride.

The starting compound required for methods A to D are, to a large extent, known compounds or may be prepared by known methods.

For instance, a compound of the formula II may be obtained by reacting a corresponding N-methyl derivative with cyanogen bromide to form the analogous N-cyano-northebaine which is then hydrolized under alkaline conditions; depending upon the hydrolysis conditions, the nor-compound of the formula II where $R_1$ is either methyl or hydrogen is obtained, that is, alkaline hydrolysis under more severe conditions simultaneously splits off the O-methyl group.

A compound of the formula VI may be obtained by reacting a compound of the formula II with an acyl halide of the formula

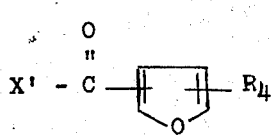

wherein $R_4$ has the meanings previously defined and $X'$ is halogen, preferably chlorine. Likewise, a compound of the formula Va may be obtained by reacting a Diels-Alder adduct of a nor-compound of the formula

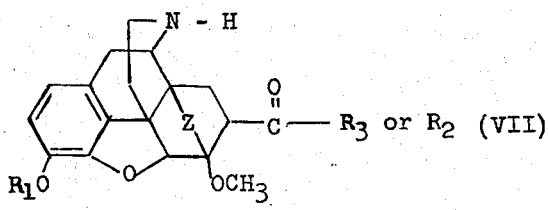

wherein $R_1$, $R_2$, $R_3$ and Z have the meanings previously defined, with an acyl halide of the formula VI.

The 6,14 — endoetheno derivatives of compounds of the formulas II, V, Va and VII (where Z is —CH=CH—) may readily be converted into the corresponding saturated 6,14-endoethano-derivatives (where Z is —CH$_2$—CH$_2$—) by catalytic hydrogenation.

The compounds embraced by formula III, IV and VI are all known compounds, and many of them are readily available in commerce.

The compounds of the formula I are bases and therefore from acid addition salts with inorganic or organic acids. Examples of non-toxic, pharmacologically acceptable acid addition salts are those formed with hydrochloric acid, sulfuric acid, phosphoric acid, nitric acid, acetic acid, propionic acid, buryric acid, valeric acid, pivalic acid, caproic acid, oxalid acid, malonic acid, succinic acid, maleic acid, fumaric acid, lactic acid, tartaric acid, citric acid, malic acid benzoic acid, phthalic acid, cinnamic acid, salicylic acid, ascorbic acid, 8-chlorotheophylline, methane-sulfonic acid, ethanephosphonic acid or the like.

The following examples illustrate the preparation of various compounds of the formula I and non-toxic addition salts thereof.

EXAMPLE 1

N-Furfuryl-6,14-endoetheno-7α-(1'-hydroxy-1'-methyl-ethyl)tetrahydro-nororipavine and its hydrochloride by method A A mixture consisting of 3.69 gm (0.01 mol) of 6,14-endoetheno-7α-(1'-hydroxy-1'-methyl-ethyl)-tetrahydro-nororipavine, 1.26 gm (0.015 mol) of sodium bicarbonate, 1.28 gm (0.011 mol) of furfuryl chloride and 35 ml of a 2:1-mixture of tetrahydrofuran and dimethylformamide was refluxed for 5 hours, accompanied by stirring. Thereafter, the reaction solution was evaporated in vacuo, the residue was shaken with a mixture of methylene chloride and water, and the organic phase was separated, washed twice with water, dried over sodium sulfate and evaporated. The residue, the free base N-furfuryl-6,14-endoetheno-7α-(1'-hydroxy-1'-methyl-ethyl)-tetrahydro-nororipavine, was dissolved in 20 ml of absolute ethanol, the resulting solution was acidified with 2 ml of 5N hydrochloric acid, the acidic solution was carefully admixed with ether, and the precipitate formed thereby was collected. 2.4 gm (49.3% of theory) of the hydrochloride of the formula

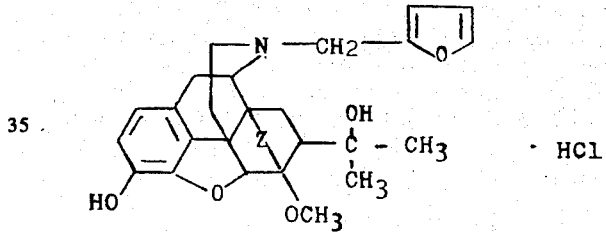

where Z is —CH=CH—, with a melting point of 224°–226° C. were obtained.

EXAMPLE 2

Using a procedure analogous to that described in Example 1, 46% of theory of N-furfuryl-6,14-endoetheno-7α-(hydroxy-methyl)-tetrahydro-northebaine, m. p. 113°–116° C., was obtained from 6,14-endetheno-northebaine, m.p. 113°–116° C., was obtained from 6,14Endetheno-7α-(hydroxy-methyl)-tetrahydro-northebaine and furfuryl chloride.

EXAMPLE 3

Using a procedure analogous to that described in Example 1, N-furfuryl-6,14-endoetheno-7α-(hydroxymethyl)tetrahydro-nororipavine and 35% of theory of its hydrochloride, m. p. 212°–218° C., were obtained from 6,14-endoetheno-7α-(hydroxy-methyl)-tetrahydro-nororipavine and furfuryl chloride.

EXAMPLE 4

Using a procedure analogous to that described in Example 1, N-(3'-furylmethyl)-6,14-endoetheno-7α-(hydroxymethyl)-tetrahydro-northebaine and 51% of theory of its hydrochloride, m. p. 254°–256° C., were obtained from 6,14-endoetheno-7α-(hydroxy-methyl)-tetrahydro-northebaine and 3-chloromethyl-furan.

EXAMPLE 5

Using a procedure analogous to that described in Example 1, N-(3'-furylmethyl)-6,14-endoetheno-7α-(hydroxymethyl)-tetrahydro-nororipavine and 35% of theory of its hydrochloride, m. .p. 222°–227° C., were obtained from 6,14-endoetheno-7α-(hydroxy-methyl)-tetrahydro-nororipavine and 3-chloromethyl-furan.

EXAMPLE 6

Using a procedure analogous to that described in Example 1, N-(2'-methyl-3'-furylmethyl)-6,14-endoetheno-7α-(hydroxy-methyl)-tetrahydro-northebaine and 46% of theory of its hydrochloride, m. p. 252° C., were obtained from 6,14-endoetheno-7α-(hydroxy-methyl)-tetrahydro-northebaine and 2-methyl-3-chloromethyl-furan.

EXAMPLE 7

Using a procedure analogous to that described in Example 1, N-(2'-methyl-3'-furylmethyl)-6,14-endoetheno-7α-(hydroxy-methyl)-tetrahydro-nororipavine and 51% of theory of its hydrochloride, m. p. 220°–225° C., were obtained from 6,14-endoetheno-7α-(hydroxy-methyl)-tetrahydro-nororipavine and 2-methyl-3-chloromethyl-furan.

EXAMPLE 8

Using a procedure analogous to that described in Example 1, N-(3'-furylmethyl)-6,14-endoetheno-7α-(1''-hydroxyethyl)-tetrahydro-northebaine and 55% of theory of its hydrochloride, m. p. 237°–240° C., were obtained from 6,14-endoetheno-7α-(1'-hydroxy-ethyl)-tetrahydro-northebaine and 3-chloromethyl-furan.

EXAMPLE 9

Using a procedure analogous to that described in Example 1, N-(3'-furylmethyl)-6,14-endoetheno-7α-(1''-hydroxyethyl)-tetrahydro-nororipavine and 56.5% of theory of its hydrochloride, m. p. 250°–252° C., were obtained from 6,14-endoetheno-7α-(1'-hydroxy-ethyl)-tetrahydro-nororipavine and 3-chloromethyl-furan.

EXAMPLE 10

Using a procedure analogous to that described in Example 1, 45% of theory of N-furfuryl-6,14-endoetheno-7α-(1'-hydroxy-ethyl)-tetrahydro-northebaine, m. p. 112°–114° C., was obtained from 6,14-endoetheno-7α-(1'-hydroxy-methyl)tetrahydro-northebaine and furfuryl chloride.

EXAMPLE 11

Using a procedure analogous to that described in Example 1, N-furfuryl-6,14-endoetheno-7α-(1'-hydroxy-ethyl)tetrahydro-nororipavine and 59.6% of theory of its hydrochloride, m. p. 242°–244° C., were obtained from 6,14-endoetheno 7α-(1'-hydroxy-ethyl)-tetrahydro-nororipavine and furfuryl chloride.

EXAMPLE 12

Using a procedure analogous to that described in Example 1, N-(2'-methyl-3'-furylmethyl)-6,14-endoetheno-7α-(1''-hydroxy-ethyl)-tetrahydro-northebaine and 60% of theory of its hydrochloride, m. p. 170° C., were obtained from 6,14-endoetheno-7α-(1'-hydroxy-ethyl)-tetrahydro-northebaine and 2-methyl-3-chloromethyl-furan.

EXAMPLE 13

Using a procedure analogous to that described in Example 1, N-(2'-methyl-3'-furylmethyl)-6,14-endoetheno-7α-(1''-hydroxy-ethyl)-tetrahydro-nororipavine and 48% of theory of its hydrochloride, m. p. 180° C., were obtained from 6,14-endoetheno-7α-(1'-hydroxy-ethyl)-tetrahydro-nororipavine and 2-methyl-3-chloromethyl-furan.

EXAMPLE 14

Using a procedure analogous to that described in Example 1, 52% of theory of N-(3'-furylmethyl)-6,14-endoethano-7α-(1''-hyroxy-ethyl)-tetrahydro-northebaine, m. p. 100°–102° C., of the formula

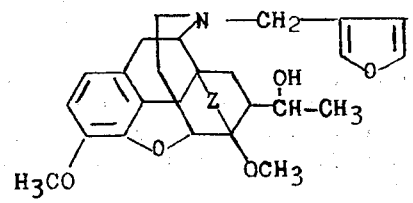

where Z is —CH$_2$—CH$_2$—, were obtained from 6,14-endoethano-7α-(1'-hydroxy-ethyl)-tetrahydro-northebaine and 3-chloromethylfuran.

EXAMPLE 15

Using a procedure analogous to that described in Example 1, N-(3'-furylmethyl)-6,14-endoethano-7α-(1''-hydroxyethyl)-tetrahydro-nororipavine and 46% of theory of its hydrochloride, m. p. 198° C., were obtained from 6,14-endoethano-7α-(1'-hydroxy-ethyl)-tetrahydro-nororipavine and 3-chloromethyl-furan.

EXAMPLE 16

Using a procedure analogous to that described in Example 1, 67% of theory of N-furfuryl-6,14-endoethano-7α-(1'-hydroxy-ethyl)-tetrahydro-northebaine, m. p. 127°–128° C., were obtained from 6,14-endoethano-7α-(1'-hydroxy-ethyl)tetrahydro-northebaine and furfuryl chloride.

EXAMPLE 17

Using a procedure analogous to that described in Example 1, N-furfuryl-6,14-endoethano-7α-(1'-hydroxy-ethyl)tetrahydro-nororipavine and 48% of theory of its hydrochloride, m.p. 250°–252° C., were obtained from 6,14-endoethano-7α(1'-hydroxy-ethyl)-tetrahydro-nororipavine and furfuryl chloride.

EXAMPLE 18

Using a procedure analogous to that described in Example 1, N-(2'-methyl-3'-furylmethyl)-6,14-endoethano-7α-(1''-hydroxy-ethyl)-tetrahydro-northebaine and 60% of theory of its hydrochloride, m.p. 175° C., were obtained from 6,14-endoethano-7α-(1'-hydroxy-ethyl)-tetrahydro-northebaine and 2-methyl-3-chloromethyl-furan.

EXAMPLE 19

Using a procedure analogous to that described in Example 1, N-(2'-methyl-3'-furylmethyl)-6,14-endoethano-7α-(1''-hydroxy-ethyl)-tetrahydro-nororipavine and 40% of theory of its hydrochloride, m. p. 250°–255° C., were obtained from 6,14-endoethano-7α-(1'-hydroxy-ethyl)-tetrahydro-nororipavine and 2-methyl-3-chloromethyl-furan.

EXAMPLE 20

Using a procedure analogous to that described in Example 1, 87.5% of theory of N-furfuryl-6,14-endoetheno-7α-(α-hydroxy-benzyl)-tetrahydro-northebaine, m.p. 179°–180° C, was obtained from 6,14-endoetheno-7α-(α-hydroxy-benzyl)-tetrahydro -northebaine and furfuryl chloride.

EXAMPLE 21

Using a procedure analogous to that described in Example 1, N-(3'-furylmethyl)-6,14-endoetheno-7α-(1''-hydroxy-1''-methyl-ethyl)-tetrahydro-northebaine and 46% of theory of its hydrochloride, m.p. 208°–212° C, were obtained from 6,14-endoetheno-7α-(1'-hydroxy-1'-methyl-ethyl)-tetrahydro-northebaine and 3-chloromethyl-furan.

EXAMPLE 22

Using a procedure analogous to that described in Example 1, N-(3'-furylmethyl)-6,14-endoetheno-7α-(1''-hydroxy-1''-methyl-ethyl)-tetrahydro-nororipavine and 63% of theory of its hydrochloride, m.p. 215°–218° C, were obtained from 6,14-endoetheno-7α-(1'-hydroxy-1'-methyl-ethyl)-tetrahydro-nororipavine and 3-chloromethyl-furan.

EXAMPLE 23

Using a procedure analogous to that described in Example 1, 68% of theory of N-furfuryl-6,14-endoetheno-7α-(1'-hydroxy-1'-methyl-ethyl)-tetrahydro-northebaine, m.p. 108°–113° C, was obtained from 6,14-endoetheno7α-(1'-hydroxy-1'-methyl-ethyl)-tetrahydro-northebaine and furfuryl chloride.

EXAMPLE 24

Using a procedure analogous to that described in Example 1, N-(2'-methyl-3'-furylmethyl)-6,14-endoetheno-7α-(1''-hydroxy-1''-methyl-ethyl)-tetrahydro-northebaine and 58% of theory of its hydrochloride, m.p. 190°–192° C, were obtained from 6,14-endoetheno-7α-(1'-hydroxy-1'-methyl-ethyl)-tetrahydro-northebaine and 2-methyl-3-chloromethyl-furan.

EXAMPLE 25

Using a procedure analogous to that described in Example 1, N-(2'-methyl-3'-furylmethyl)-6,14-endoetheno-7α-(1''-hydroxy-1''-methyl-ethyl)-tetrahydro-nororipavine and 72.5% of theory of its hydrochloride, m.p. 215°–218° C, were obtained from 6,14-endoetheno-7α-(1'-hydroxy-1'-methyl-ethyl)-tetrahydro-nororipavine and 2-methyl-3-chloromethyl-furan.

EXAMPLE 26

Using a procedure analogous to that described in Example 1, N-(3'-furylmethyl)-6,14-endoethano-7α-(1''-hydroxy-1''-methyl-ethyl)-tetrahydro-northebaine and 46% of theory of its hydrochloride, m.p. 220°–223° C, were obtained from 6,14-endoethano-7α-(1'-hydroxy-1'-methyl-ethyl)-tetrahydro-northebaine and 3-chloromethyl-furan.

EXAMPLE 27

Using a procedure analogous to that described in Example 1, N-(3'-furylmethyl)-6,14-endoethano-7α-(1''-hydroxy-1''-methyl-ethyl)-tetrahydro-nororipavine and 60.2% of theory of its hydrochloride, m.p. 215°–220° C, were obtained from 6,14-endoethano-7α-(1'-hydroxy-1'-methyl-ethyl)-tetrahydro-nororipavine and 3-chloromethyl-furan.

EXAMPLE 28

Using a procedure analogous to that described in Example 1, 48.7% of theory of N-furfuryl-6,14-endoethano-7α-(1'-hydroxy-1'-methyl-ethyl)-tetrahydro-northebaine, m.p. 130°–1330° C, was obtained from 6,14-endoethano-7α-(1'-hydroxy-1'-methyl-ethyl)-tetrahydro-northebaine and furfuryl chloride.

EXAMPLE 29

Using a procedure analogous to that described in Example 1, N-furfuryl-6,14-endoethano-7α-(1'-hydroxy-1'-methyl-ethyl)-tetrahydro-nororipavine and 63.2% of theory of its hydrochloride, m.p. 215°–220° C, were obtained from 6,14-endoethano-7α-(1'-hydroxy-1'-methyl-ethyl)-tetrahydro-nororipavine and furfuryl chloride.

EXAMPLE 30

Using a procedure analogous to that described in Example 1, N-(2'-methyl-3'-furylmethyl)-6,14-endoethano-7α-(1''-hydroxy-1''-methyl-ethyl)-tetrahydro-northebaine and 73.4% of theory of its hydrochloride, m.p. 158°–187° C, were obtained from 6,14-endoethano-7α-(1'-hydroxy-1'-methyl-ethyl)-tetrahydro-northebaine and 2-methyl-3-chloromethyl-furan.

EXAMPLE 31

Using a procedure analogous to that described in Example 1, N-(2'-methyl-3'-furylmethyl-6,14-endoethano-7α-(1''-hydroxy-1''-methyl-ethyl)-tetrahydro-nororipavine and 44% of theory of its hydrochloride, m.p. 218°–222° C, were obtained from 6,14-endoethano-7α-(1'-hydroxy-1'-methyl-ethyl)-tetrahydro-nororipavine and 2-methyl-3-chloromethyl-furan.

EXAMPLE 32

Using a procedure analogous to that described in Example 1, N-(3'-furylmethyl)-6,14-endoetheno-7α-(1''-hydroxy-1''-methyl-n-butyl)-tetrahydro-northebaine and 61% of theory of its hydrochloride, m.p. 190°–193° C, were obtained from 6,14-endoetheno-7α-(1'-hydroxy-1'-methyl-n-butyl)-tetrahydro-northebaine and 3-chloromethyl-furan.

EXAMPLE 33

Using a procedure analogous to that described in Example 1, N-(3'-furylmethyl)-6,14-endoetheno-7α-(1''-hydroxy-1''-methyl-n-butyl)-tetrahydro-nororipavine and 42% of theory of its hydrochloride, m.p. 200°–207° C, were obtained from 6,14-endoetheno-7α-(1'-hydroxy-1'-methyl-n-butyl)-tetrahydro-nororipavine and 3-chloromethyl-furan.

EXAMPLE 34

Using a procedure analogous to that described in Example 1, N-furfuryl-6,14-endoetheno-7α-(1'-hydroxy-1'-methyl-n-butyl)-tetrahydro-northebaine and 75.8% of theory of its hydrochloride, m.p.

160°–165° C, were obtained from 6,14-endoetheno-7α-(1'-hydroxy-1'-methyl-n-butyl)-tetrahydro-northebaine and furfuryl chloride.

EXAMPLE 35

Using a procedure analogous to that described in Example 1, N-furfuryl-6,14-endoetheno-7α-(1'-hydroxy-1'-methyl-n-butyl)-tetrahydro-nororipavine and 54.5% of theory of its hydrochloride, m.p. 185°–187° C, were obtained from 6,14-endoetheno-7α-(1'-hydroxy-1'-methyl-n-butyl)-tetrahydro-nororipavine and furfuryl chloride.

EXAMPLE 36

Using a procedure analogous to that described in Example 1, N-(2'-methyl-3'-furylmethyl)-6,14-endoetheno-7α-(1''-hydroxy-1''-methyl-n-butyl)-tetrahydro-northebaine and 49.4% of theory of its hydrochloride, m.p. 196°–198° C, were obtained from 6,14-endoetheno-7α-(1'-hydroxy-1'-methyl-n-butyl)-tetrahydro-northebaine and 2-methyl-3-chloromethylfuran.

EXAMPLE 37

Using a procedure analogous to that described in Example 1, 47.5% of theory of N-(2'-methyl-3'-furylmethyl)-6,14-endoetheno-7α-(1''-hydroxy-1''-methyl-n-butyl)-tetrahydro-nororipavine, m.p. 220°–222° C, was obtained from 6,14-endoetheno-7α-(1'-hydroxy-1'-methyl-n-butyl)-tetrahydro-nororipavine and 2-methyl-3-chloromethyl-furan.

EXAMPLE 38

Using a procedure analogous to that described in Example 1, N-furfuryl-6,14-endoethano-7α-(1'-hydroxy-1'-methyl-n-butyl)-tetrahydro-northebaine and 42.8% of theory of its hydrochloride, m.p. 154°–156° C, were obtained from 6,14-endoethano-7α-(1'-hydroxy-1'-methyl-n-butyl)-tetrahydro-northebaine and furfuryl chloride.

EXAMPLE 39

Using a procedure analogous to that described in Example 1, N-(3'-furylmethyl)-6,14-endoethano-7α-(1''-hydroxy-1''-methyl-n-butyl)-tetrahydro-northebaine and 74% of theory of its hydrochloride, m.p. 218° C, were obtained from 6,14-endoethano-7α-(1'-hydroxy-1'-methyl-n-butyl)-tetrahydro-northebaine and 3-chloromethyl-furan.

EXAMPLE 40

Using a procedure analogous to that described in Example 1, N-(2'-methyl-3'-furylmethyl)-6,14-endoethano-7α-(1''-hydroxy-1''-methyl-n-butyl)-tetrahydro-northebaine and 75.8% of theory of its hydrochloride, m.p. 172°–174° C, were obtained from 6,14-endoethano-7α-(1'-hydroxy-1'-methyl-n-butyl)-tetrahydro-northebaine and 2-methyl-3-chloromethylfuran.

EXAMPLE 41

Using a process analogous to that described in Example 1, 66.7% of theory of N-(3'-furylmethyl)-6,14-endoetheno-7α-(1''-hydroxy-1''-methyl-3''-phenyl-n-propyl)-tetrahydro-northebaine, m.p. 170°–172° C, was obtained from 6,14-endoetheno-7α-(1'-hydroxy-1'-methyl-3'-phenyl-n-propyl)tetrahydro-northebaine and 3-chloromethyl-furan.

EXAMPLE 42

Using a procedure analogous to that described in Example 1, 52% of theory of N-(3'-furylmethyl)-6,14-endoetheno-7α-(1''-hydroxy-1''-methyl-3''-phenyl-n-propyl)-tetrahydro-nororipavine, m.p. 245°–247° C, was obtained from 6,14-endoetheno-7α-(1'-hydroxy-1'-methyl-3'-phenyl-n-propyl)tetrahydro-nororipavine and 3-chloromethyl-furan.

EXAMPLE 43

Using a procedure analogous to that described in Example 1, N-furfuryl-6,14-endoetheno-7α-(1'-hydroxy-1'-methyl-3'-phenyl-n-propyl)-tetrahydro-northebaine and 57.7% of theory of its hydrochloride, m.p. 169°–171° C, were obtained from 6,14-endoetheno-7α-(1'-hydroxy-1'-methyl-3'-phenyl-n-propyl)-tetrahydro-northebaine and furfuryl chloride.

EXAMPLE 44

Using a procedure analogous to that described in Example 1, 74% of theory of N-furfuryl-6,14-endoetheno-7α-(1'-hydroxy-1'-methyl-3'-phenyl-n-propyl)-tetrahydro-nororipavine, m.p. 222°–224° C, was obtained from 6,14-endoetheno-7α-(1'-hydroxy-1'-methyl-3'-phenyl-n-propyl)-tetrahyro-nororipavine and furfuryl chloride.

EXAMPLE 45

Using a procedure analogous to that described in Example 1, N-(2'-methyl-3'-furylmethyl)-6,14-endoetheno-7α-(1''-hydroxy-1''-methyl-3''-phenyl-n-propyl)-tetrahydro-northebaine and 56.7% of theory of its hydrochloride, m.p. 165°–169° C, were obtained from 6,14-endoetheno-7α-(1'-hydroxy-1'-methyl-3'-phenyl-n-propyl)-tetrahydro-northebaine and 2-methyl-3-chloromethyl-furan.

EXAMPLE 46

Using a procedure analogous to that described in Example 1, N-(2'-methyl-3'-furylmethyl)-6,14-endoetheno-7α-(1''-hydroxy-1''-methyl-3''-phenyl-n-propyl)-tetrahydro-nororipavine and 40% of theory of its hydrochloride, m.p. 232°–234° C, were obtained from 6,14-endoetheno-7α-(1'-hydroxy-1'-methyl-3'-phenyl-n-propyl)-tetrahydro-nororipavine and 2-methyl-3-chloromethyl-furan.

EXAMPLE 47

N-(5'-Methyl-furfuryl)-6,14-endoetheno-7α-(1''-hydroxy-1''-methyl-ethyl)-tetrahydro-nororipavine and its hydrochloride by method B 3.69 gm (0.01 mol) of 6,14-endoetheno-7α-(1'-hydroxy-1'-methyl-ethyl)-tetrahydro-nororipavin were dissolved in 10 ml of aqueous 50% acetic acid, and, while stirring the resulting solution, it was admixed with 1.0 gm of aqueous 30% formaldehyde (0.01 mol formaldehyde). Subsequently, while stirring, 0.82 gm (0.01 mol) of 2-methyl-furan was slowly added dropwise to the mixture, and the resulting mixtuure was then stirred for 15 hours at room temperature. Thereafter, the reaction mixture was made alkaline with concentrated ammonia while adding ice, then it was extracted with methylene chloride, and the organic phase was washed several times with water, dried over sodium sulfate and evaporated. The residue, the free base N-(5'-methyl-furfuryl)-6,14-endoetheno-7α-(1''- hydroxy-1″-methyl-ethyl)-tetrahydro-nororipavin, was dissolved in ethanol, the solution was acidified with ethanolic hydrochloric acid, and ether was added until the solution began to turn cloudy. The precipitate formed thereby was collected, yielding 3.2 gm (62% of theory) of the hydrochloride which had a melting point of 191°–195° C.

EXAMPLE 48

N-(3′-Methyl-furfuryl)-6,14-endoetheno-7α-(1″-hydroxy-1″-methyl-ethyl)-tetrahydro-nororipavine and its hydrochloride by method C 3.69 gm (0.01 mol) of 6,14-endoetheno-7α-(1′-hydroxy-1′-methyl-ethyl)-tetrahydro-nororipavine were suspended in 35 ml of methanol, the suspension was admixed with a solution of 2.5 gm of potassium carbonate in 4 ml of water, and then, while cooling the mixture, 1.74 gm (0.011 mol) of 3-methylfuran-2-carboxylic acid chloride were added dropwise over a period of 20 minutes, and the resulting mixture was stirred for 3 hours. Thereafter, the reaction mixture was evaporated in vacuo, the residue was dissolved in methylene chloride, and the resulting solution hydrochloric acid, dilute sodium bicarbonate solution and again with water. The organic phase was dried over sodium sulfate, evaporated in vacuo, the residue was dissolved in 50 ml of absolute tetrahyrofuran, the resulting solution was added dropwise to a solution of 0.76 gm (0.02 mol) of lithium aluminum hydride in 25 ml of tetrahydrofuran at 5° to 10° C, and the mixture was stirred overnight at room temperature. Thereafter, the resulting suspension was carefully admixed with 1.5 ml of water while cooling on ice, then 75 ml of saturated aqueous diammonium tartrate were added, and the mixture was allowed to stand for 1 hour. The tetrahydrofuran (upper) phase was separated and evaporated, the aqueous phase was extracted twice with methylene chloride, the residue of the tetrahydrofuran phase evaporation was dissolved and the combined methylene chloride extracts, and the resulting solution was washed several times with water, dried, over sodium sulfate and evaporated in vacuo. The residue, the free base N-(3′-methyl-furfuryl)-6,14-endoetheno-7α-(1″-hydroxy-1″-methyl-ethyl)-tetrahydro-nororipavine, was dissolved in ethanol, the solution was acidified with etherereal hydrochloric acid, and the crystalline substance which separated out was collected, yielding 2.2 gm (45% of theory) of the hydrochloride which had a melting pont of 195° C.

EXAMPLE 49

Using a procedure analogous to that described in Example 48, N-(3′-methyl-furfuryl)-6,14-endoetheno-7α-(1″-hydroxy-ethyl)-tetrahydro-northebaine and 60.4% of theory of its hydrochloride, m.p. 165°–169° C, were obtained from 6,14-endoetheno-7α-(1′-hydroxy-ethyl)-tetrahydro-northebained and 3-methyl-furoyl chloride, and subsequent reduction of the intermediate with lithium aluminum hydride,

EXAMPLE 50

Using a procedure analogous to that described in Example 48, N-(3′-methyl-furfuryl)-6,14-endoetheno-7α-(1″-hydroxy-ethyl)-tetrahydro-nororipavine and 77.6% of theory of its hydrochloirde, m.p. 230°–232° C, were obtained from 6,14-endoetheno-7α-(1′-hydroxy-ethyl)-tetrahydro-nororipavine and 3-methyl-furoyl chloride, and subsequent reduction of the intermediate with lithium aluminum hydride.

EXAMPLE 51

Using a procedure analogous to that describied in Example 48, N-(3′-methyl-furfuryl)-6,14-endoethano-7α-(1″-hydroxy-ethyl)-tetrahydro-northebaine and 64.4% of theory of its hydrochloride, m.p. 190°–102° C, were obtained from 6,14-endoethano-7α-(1′-hydroxy-ethyl)-tetrahydro-northebaine and 3-methyl-furoyl chloride, and subsequent reduction of the intermediate with lithium aluminum hydride.

EXAMPLE 52 using a procedure analogous to that described in Example 48 N-(3′-methyl-furfuryl)-6,14-endoethano-7α-(1″-hydroxy-ethyl)-tetrahydro-nororipavine and 47.6% of theory of its hydrochloride, m.p. 230°–235° C, were obtained from 6,14-endoethano-7α-(1′-hydroxy-ethyl)-tetrahydro-nororipavine and 3-methyl-furoyl chloride, and subsequent reduction of the intermediate with lithium aluminum hydride.

EXAMPLE 53

Using a procedure analogous to that described in Example 48, N-(3′-methyl-furfuryl)-6,14-endoetheno-7α-(1″-hydroxy-1″-methyl-ethyl)-tetrahydro-northebaine and 62.3% of theory of its hydrochlodride, m.p. 170°–172°C, were obtained from 6,14-endoetheno-7α-(1′-hydroxy-1′-methyl-ethyl)-tetrahydro-northebaine and 3-methyl-furoyl chloride, and subsequent reduction of the intermediate with lithium aluminum hydride.

EXAMPLE 54

Using a procedure analogous to that described in Example 48, N-(3′-methyl-furfuryl)-6,14-endoethano-7α-(1″-hydroxy-1″-methyl-ethyl)-tetrahydro-northebaine and 53% of theory of its hyrochloride, m.p. 155°–157° C, were obtained from 6,14-endoethano-7α-(1′-hydroxy-1′-methyl-ethyl)-tetrahydro-northebaine and 3-methyl-furoyl chloride, and subsequent reduction of the intermediate with lithium aluminum hydride.

EXAMPLE 55

Using a procedure analogous to that described in Example 48, N-(3′-methyl-furfuryl)-6,14-endoethano-7α-(1″-hydroxy-1″-methyl-ethyl)-tetrahydro-nororipavine and 72.5% of theory of its hydrochloride, m.p. 210°–212° C, were obtaind from 6,14-endoethano-7α-(1′-hydroxy-1′-methyl-ethyl)-tatrahydro-nororipavine and 3-methyl-furoyl chloride, and subsequent reduction of the intermediate with lithium aluminum hydride.

EXAMPLE 56

Using a procedure analogous to that described in Example 48, N-(3′-methyl-furfuryl)-6,14-endoetheno-7α-(1″-hydroxy-1″-methyl-n-butyl)-tetrahydro-northebaine and 71.2% of theory of its hydrochloride, m.p. 170°–172° C, were obtained from 6,14-endoetheno-7α-(1′-hydroxy-1′-methyl-n-butyl)-tetrahydro-northebaine and 3-methyl-furoyl chloride, and subsequent reduction of the intermediate with lithium aluminum hydride.

EXAMPLE 57

Using a procedure analogous to that described in Example 48, 59.4% of theory of N-(3'-methyl-furfuryl)-6,14-endoetheno-7α-(1''-hydroxy-1''-methyl-n-butyl)-tetrahydro-nororipavine, m.p. 204°–206° C, was obtained from 6,14-endoetheno-7α-(1'-hydroxy-1'-methyl-n-butyl)-tetrahydro-nororipavine and 3-methyl-furoyl chloride, and subsequent reduction of the intermediate with lithium aluminum hydride.

EXAMPLE 58

Using a procedure analogous to that described in Example 48, N-(3'-methyl-furfuryl)-6,14-endoethano-7α-(1''-hydroxy-1''-methyl-n-butyl)-tetrahydro-northebaine and 56.8% of theory of its hydrochloride, m.p. 155°–159° C, were obtained from 6,14-endoethano-7α-(1'-hydroxy-1'-methyl-n-butyl)-tetrahydrdo-northebaine and 3-methyl-furoyl chloride, and subsequent reduction of the intermediate with lithium aluminum hydride.

EXAMPLE 59

Using a procedure analogous to that described in Example 48, N-(3'-methyl-furfuryl)-6,14-endoetheno-7α-(1''-hydroxy-1''-methyl-3''-phenyl-n-propyl)-tetrahydro-northebaine and 56.7% of theory of its hydrochloride, m.p. 211° C, were obtained from 6,14-endoetheno-7α-(1'-hydroxy-1'-methyl-3'-phenyl-n-propyl)-tetrahydro-northebaine and 3-methyl-furoyl chloride, and subseqent reduction of the intermediate with lithium aluminum hydride.

EXAMPLE 60

Using a procedure analogous to that described in Example 48, N-(3'-methyl-furfuryl)-6,14-endoetheno-7α-(1''-hydroxy-1''-methyl-3''-phenyl-n-propyl)-tetrahydror-nororipavine and 61% of theory of its hydrochloride, m.p. 247°–248° C, were obtained from 6,14-endoetheno-7α-(1'-hydroxy-1'-methyl-3'-phhenyl-n-propyl)-tetrahydro-nororipavine and 3-methyl-furoyl chloride, and subsequent reduction of the intermediate with lithium aluminum hydride.

EXAMPLE 61

Using a procedure analogous to that described in Example 43, N-(3'-methyl-furfuryl)-6,14-endoetheno-7α-(1''-hydroxy-methyl)-tetrahydro-northebaine and 33% of theory of its hydrochloride, m.p. 200°–202° C, were obtained from 6,14-endoetheno-7α-(1''-hydroxy-methyl)-tetrahydro-northebaine and 3-methyl-furoyl chloride, and subsequent reduction of the intermediate with lithium aluminum hydride.

EXAMPLE 62

Using a procedure analogous to that described in Example 48, N-(3'-methyl-furfuryl)-6,14-endoetheno-7α-(1''-hydroxy-methyl)-tetrahydro-nororipavine and 34% of theory of its hydrochloride, m.p. 195°–199° C, were obtained from 6,14-endoetheno-7α-(1''-hydroxy-methyl)-tetrahydro-nororipavine and 3-methyl -furoyl chloride, and subsequent reduction of the intermedate with lithium aluminum hydride.

EXAMPLE 63

N-Furfuryl-3-(O-acetyl)-6,14-endoetheno-7α-(1'-hydroxy-1'-methyl-ethyl)-tetrahydro-nororipavine by method D A mixture consisting of 4.46 gm (0.01 mol) of N-furfuryl-6,14-endoetheno-7α-(1'-hydroxy-1'-methyl-ethyl)tetrahydro-nororipavine, 10 ml of acetic acid anhydride and 0.82 gm (0.1 mol) of sodium acetate was heated for 1 hour at 100° C. Thereafter, the reaction mixture was allowed to cool, was then poured over 100 gm of ice, and after an intersection of 5 minutes the aqueous mixture was made distinctly alkaline with aqueous 30% sodium hydroxide. The resulting suspension was extracted with methylene chloride, and the organic extract solution was washed several times with water, dried over sodium sulfate and evaporated, yielding 3 gm (62.5% of theory) of the compound of the formula

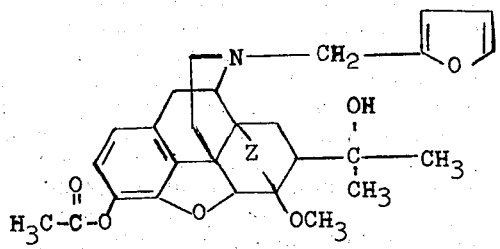

where Z is —CH—CH—, which had a melting point of 122°–123° C (recrystallized from petroleum ether).

The compounds embraced by formula I and their nontoxic, pharmacologically acceptable acid addition salts, have useful pharmacodynamic properties. More particularly, they exhibit non-narcotic analgesic and antitussive activities in warm-blooded animals such as mice and rats.

All of the compounds of the formula I and their non-toxic salts proved to be ineffective as analgesics in the Haffner test for analgesia [Duetsche Medizinische Wochenschrift 55, 731 (1929)] on mice and rats.

On the other hand, they exhibit a distinct, dose-dependent analgesic activity in more sensitive pharmacological tests for analgesia, such as the hot-plate test [J. Pharmacoo. Exp. Therap. 80, 300 (1944)] or the writhing test [J. Pharmacol. Exp. Therap. 154, 319 (1966)].

In accordance with the presently prevailing teachings [Adv. Chem. Soc. 49, 162–169 (1964)], inactivity in the Haffner test is indicative of non-narcotic properties, while activity in the hot-plate test and/or writhing test proves analgesic properties.

For pharmaceutial purposes the compounds of the formula I or their non-toxic acid addition salts are administered to warm-blooded animals perorally, enterally or parenterally as ative ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective oral analgesic and antitussive dosage unit of the compounds of the formula I and their non-toxic acid addition salts is from 0.016 to 6.7 mgm/kg body weight, preferably 0.41 to 3.4 mgm/kg body weight.

The following examples illustrate a few pharmaceutical dosage unit compositions comprising a compound of the formula I or a non-toxic pharmacologically acceptable acid addition salt thereof as an active ingredient and represent the best modes contemplated of putting the invention into practical use. The parts are parts by weight unless otherwise specified.

EXAMPLE 64

Tablets

The tablet composition is compounded from the following ingredients:

| | |
|---|---|
| N-Furfuryl-7$\alpha$-(hydroxy-methyl)-6,14-endoetheno-tetrahydro-northebaine | 50.0 parts |
| Lactose | 95.0 parts |
| Corn starch | 45.0 parts |
| Colloidal silicic acid | 2.0 parts |
| Soluble starch | 5.0 parts |
| Magnesium stearate | 3.0 parts |
| Total | 200.0 parts |

Preparation:

The northebaine compound is intimately admixed with the lactose and the corn starch, the mixture is moistened with an aqueous 10% solution of the soluble starch, the moist mass is forced through a 1 mm-mesh screen, the resulting granulate is dried at 40° C, the dry granulate is admixed with the colloidal silicic acid, and the composition is compressed into 200 mgm-tablets in a conventional tablet making machine. Each tablet contains 50 mgm of the northebaine compounds and is an oral dosage unit composition with effective analgesic and antitussive actions.

EXAMPLE 65

Coated Pills

The pill core composition is compounded from the following ingredients:

| | |
|---|---|
| N-Furfuryl-6,14-endoetheno-7$\alpha$-(hydroxy-methyl)-tetrahydro-nororipavine hydrochloride | 75.0 parts |
| Lactose | 100.0 parts |
| Corn starch | 65.0 parts |
| Colloidal silicic acid | 2.0 parts |
| Soluble starch | 5.0 parts |
| Magnesium stearate | 3.0 parts |
| Total | 250.0 parts |

Preparation:

The ingredients are compounded in the same manner as in Example 64, and the composition is compressed into 250 mgm-pill cores which are subsequently coated with a thin shell consisting essentially of a mixture of sugar, talcum and gum arabic and finally polished with beeswax. Each coated pill contains 75 mgm of the nororipavine compound and is an oral dosage unit composition with effective analgesic and antitussive activities.

EXAMPLE 66

Suppositories

The suppository composition is compounded from the following ingredients:

| | |
|---|---|
| N-Furfuryl-6,14-endoetheno-7$\alpha$-(1'-hydroxy-1'-methyl-ethyl)-tetrahydro-nororipavine hydrochloride | 50.0 parts |
| Lactose | 250.0 parts |
| Suppository base (e.g. cocoa butter) | 1400.0 parts |
| Total | 1700.0 parts |

Preparation:

The nororipavine compound is intimately admixed with the lactose, and the mixture is blended with the aid of an immersion homogenizer into the suppository base which had previously been melted and cooled to about 40° C. 1700 mgm-portions of the composition are poured into cooled suppository molds and allowed to harden therein. Each suppository contains 50 mgm of the noripavine compound and is a rectal dosage unit composition with effective analgesic and antitussive actions.

EXAMPLE 67

Hypodermic Solution

The solution is compounded from the following ingredients:

| | | |
|---|---|---|
| N-(2'-Methyl-3'-furylmethyl)-6,14-endoetheno-7$\alpha$-(hydroxy-methyl)-tetrahydro-nororipavine | | 75.0 parts |
| Socium chloride | | 5.0 parts |
| Double-distilled water | q.s.ad | 2000.0 parts by vol. |

Preparation:

The nororipavine compound and the sodium chloride are dissolved in the double-distilled water, the solution is filtered until free from suspended particles, and the filtrate is filled under aseptic conditions into 2 cc-ampules which are subsequently sterilized and sealed. Each sample contains 75 mgm of the nororipavine compound, and its contents are an injectable dosage unit composition with effective analgesic and antitussive actions.

EXAMPLE 68

Drop Solution

The solution is compounded from the following ingredients:

| | | |
|---|---|---|
| N-Furfuryl-6,14-endoetheno-7$\alpha$-(1'-hydroxy-1'-methyl-ethyl)-tetrahydro-nororipavine hydrochloride | | 0.80 parts |
| Methyl p-hydroxy-benzoate | | 0.60 parts |
| Propyl p-hydroxy-benzoate | | 0.04 parts |
| Demineralized water | q.s.ad | 100.0 parts by vol. |

Preparation:

The nororipavine compound and the p-hydroxy-benzoates are dissolved in the demineralized water, the solution is filtered, and the filtrate is filled into 100 ml-bottles. 10 ml of the solution contain 80 mgm of the nororipavine compound and are an oral dosage unit composition with effective analgesic and antitussive actions.

Analogous results are obtained when any one of the other compounds embraced by formula I or a non-toxic acid addition salt thereof is substituted for the particular northebaine or nororipavine compound in Examples 64 through 68. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. An analgesic or antitussive pharmaceutical dosage unit composition consisting essentially of an inert pharmaceutical carrier and an effective analgesic or antitussive amount of a compound of the formula

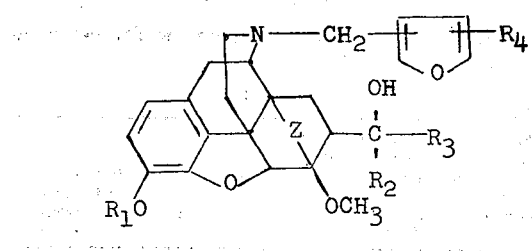

wherein
$R_1$ is hydrogen, methyl or acetyl,
$R_2$ is hydrogen or methyl,
$R_3$ is hydrogen, methyl, n-propyl, phenethyl or phenyl
$R_4$ is hydrogen or methyl, and
Z is —CH=CH— or —CH$_2$—CH$_2$—,
or a non-toxic, pharmacologically acceptable acid addition salt thereof.

2. A composition of claim 1, where said compound is of the formula

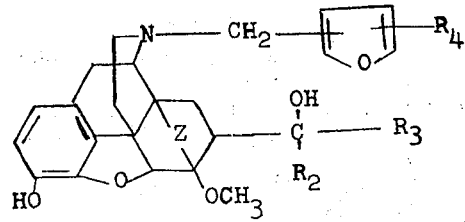

wherein
$R_2$ is hydrogen or methyl,
$R_3$ is hydrogen, methyl, n-propyl, phenethyl or phenyl,
$R_4$ is hydrogen or methyl, and
Z is —CH=CH— or —CH$_2$—CH$_2$—
or a non-toxic, pharmacologically acceptable acid addition salt thereof.

3. A composition of claim 1, where said compound is N-furfuryl-6,14-endoetheno-7α-(hydroxy-methyl)-tetrahydronorthebaine or a non-toxic, pharmacologically acceptable acid addition salt thereof.

4. A composition of claim 1, where said compound is N-furfuryl-6,14-endoetheno-7α-(hydroy-methyl)-tetrahydronororipavine or a non-toxic, pharmacologicalaly acceptable salt addition salt thereof.

5. A composition of claim 1, where said compound is N-furfuryl-6,14-endoetheno-7α-(1'-hydroxy-1'-methyl-ethyl)tetrahydro-nororipavine or a non-toxic, pharmacologically acceptable acid addition salt thereof.

6. A composition of claim 1, where said compound is N-(2'-methyl-3'-furylmethyl)-6,14-endoetheno-7α-(hydroxymethyl)-tetrahydro-nororipavine or a non-toxic, pharmacologically acceptable acid addition salt thereof.

7. The method of raising the pain threshold or suppressing the cough reflex in a warm-blooded animal, which comprises administering to said animal an effective analgesic or antitussive amount of a compound of the formula

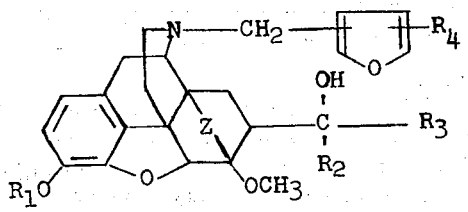

wherein
$R_1$ is hydrogen, methyl or acetyl,
$R_2$ is hydrogen or methyl,
$R_3$ is hydrogen, methyl, n-propyl, phenethyl or phenyl
$R_4$ is hydrogen or methyl, and
Z is —CH=CH— or —CH$_2$—CH$_2$—,
or a non-toxic, pharmacologically acceptable acid addition salt thereof.

8. The method of claim 7, where said compound is of the formula

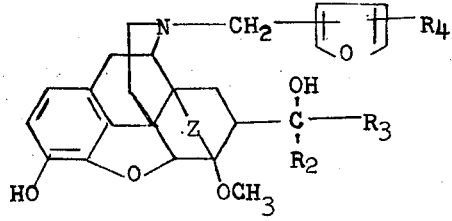

wherein
$R_2$ is hydrogen or methyl,
$R_3$ is hydrogen, methyl, n-propyl, phenethyl or phenyl
$R_4$ is hydrogen or methyl, and
Z is —CH=CH or —CH$_2$—CH$_2$—
or a not-toxic, phamacologically acceptable acid addition salt thereof.

9. The method of claim 7, where said compound is N-furfuryl-6,14-endoetheno-7α-(hydroxy-methyl)-tetrahydro-northebaine or a non-toxic, pharmacologically acceptable acid addition thereof.

10. The method of claim 7, wherein said compound is N-furfuryl-6,14-endoetheno-7α-(hydroxy-methyl)-tetrahydronororipavine or a non-toxic, pharmacologically acceptable acid addition salt thereof.

11. The method of claim 7, where said compound is N-furfuryl-6,14-endoetheno-7α-(1'-hydroxy-1'-methyl-ethyl)tetrahydro-nororipavine or a non-toxic, pharmacologically acceptable salt addition salt thereof.

12. The method of claim 7, where said compound is N-(2'-methyl-3'-furylmethyl)-6,14-endoetheno-7α-(hydroxymethyl(-tetrahydro-nororipavine or a non-toxic, pharmacologically acceptable acid addition salt thereof.

* * * * *

UNITED STATES PATENT OFFICE
CERTIFICATE OF CORRECTION

Patent No. 3,992,542     Dated November 16, 1976

Inventor(s) ADOLF LANGBEIN, HERBERT MERZ, GERHARD WALTHER and KLAUS STOCKHAUS

It is certified that error appears in the above-identified patent and that said Letters Patent are hereby corrected as shown below:

| | |
|---|---|
| Col. 3, Line 11 | "reaction" should read -- reacting -- |
| Col. 3, Line 12 | after "and" -- a -- should be inerted |
| Col. 3, Line 67 | "A" should read -- Z -- |
| Col. 5, Line 50 | " $\eta$ " should be deleted |
| Col. 6, Line 50-51 | "northebaine, m.p. 113°-116°C., was obtained from 6,14 Endetheno" should be deleted |
| Col. 10, Line 15 | "-1330°C" should read -- -133°C -- |
| Col. 11, Line 65 | "-172°C" should read -- -171°C -- |
| Col. 12, Line 55 | "-nororipavin" should read -- -nororipavine -- |
| Col. 13, Line 24-25 | after "solution" -- was washed successively several times with water, dilute -- should be inserted |
| Col. 14, Line 9 | "-102°" should read -- -192° -- |
| Col. 15, Line 4 | "59.4%" should read -- 50.4% -- |
| Col. 15, Line 41 | "rahydror-" should read -- rahydro- -- |
| Col. 15, Line 43 | "-phhenyl-" should read -- -phenyl- -- |

UNITED STATES PATENT OFFICE
CERTIFICATE OF CORRECTION

Patent No. 3,992,542                    Dated November 16, 1976

Inventor(s) ADOLF LANGBEIN, HERBERT MERZ, GERHARD WALTHER and KLAUS STOCKHAUS

It is certified that error appears in the above-identified patent and that said Letters Patent are hereby corrected as shown below:

| | | |
|---|---|---|
| Col. 15, Line 51 | "43" should read | -- 48 -- |
| Col. 15, Line 54 | "1'" should read | -- 1' -- |
| Col. 15, Line 65 | "1'" should read | -- 1' -- |
| Col. 16, Line 34 | "CH-CH" should read | -- CH=CH -- |
| Col. 16, Line 49 | "Pharmacoo." should read | -- Pharmacol. -- |
| Col. 18, Line 46 | "sample" should read | -- ampule -- |

Col. 5, line 61, after "drochloric acid", -- hydrobromic acid, hydroiodic acid, hydrofluoric acid -- should be inserted.

Signed and Sealed this

Twenty-ninth Day of March 1977

[SEAL]

Attest:

RUTH C. MASON
Attesting Officer

C. MARSHALL DANN
Commissioner of Patents and Trademarks